(12) United States Patent
Bednarkiewicz et al.

(10) Patent No.: US 9,134,236 B2
(45) Date of Patent: Sep. 15, 2015

(54) METHOD OF FLUORESCENCE IMAGING (75) Inventors: Artur Bednarkiewicz, Wroclaw (PL);
Maurice Whelan, Angera (IT)

(73) Assignee: THE EUROPEAN COMMUNITY, REPRESENTED BY THE EUROPEAN COMMISSION (BE)

( * ) Notice: Subject to any disclaimer, the term of this patent is extended or adjusted under 35 U.S.C. 154(b) by 965 days.

(21) Appl. No.: 12/601,587

(22) PCT Filed: May 30, 2008

(86) PCT No.: PCT/EP2008/056672
§ 371 (c)(1),
(2), (4) Date: Jun. 15, 2010

(87) PCT Pub. No.: WO2008/145720
PCT Pub. Date: Dec. 4, 2008

(65) Prior Publication Data
US 2010/0278399 A1 Nov. 4, 2010

(30) Foreign Application Priority Data
Jun. 1, 2007 (EP) .................................... 07109459

(51) Int. Cl.
*G06K 9/00* (2006.01)
*G01N 21/64* (2006.01)
(Continued)

(52) U.S. Cl.
CPC ........ *G01N 21/6408* (2013.01); *G01N 21/6458* (2013.01); *G02B 21/16* (2013.01); *G02B 21/365* (2013.01); *G01N 2021/6423* (2013.01); *G01N 2201/0675* (2013.01)

(58) Field of Classification Search
CPC ....................................................... G06T 7/0012
USPC .......................................................... 382/128
See application file for complete search history.

(56) References Cited

U.S. PATENT DOCUMENTS 5,485,530 A * 1/1996 Lakowicz et al. ............. 382/191
7,136,518 B2 * 11/2006 Griffin et al. ................. 382/133
2003/0148393 A1 8/2003 Woodbury et al.
(Continued)

FOREIGN PATENT DOCUMENTS

EP 1788379 5/2007
JP 2006-171024 6/2006

OTHER PUBLICATIONS

B.W. Pogue, et al.; "Fluorescence Imaging In Vivo: Raster Scanned Point-Source Imaging Provides More Accurate Quantification then Broad Beam Geometries"; Technology in Cancer Research and Treatment 3, 15-21 (2004).
(Continued)

*Primary Examiner* — Sheetal R Paulson
(74) *Attorney, Agent, or Firm* — Cantor Colburn LLP (57) ABSTRACT

Method of fluorescence imaging including: illuminating a sample to excite its fluorescence and acquiring an image thereof; based on fluorescence spectral and spatial information from the sample's fluorescence image, segmenting the image into regions of similar spectral properties; for each image segment, exciting the fluorescence of the corresponding sample region, and detecting the corresponding fluorescence; based on modelling, determining expected fluorescence parameters from the fluorescence signals detected for each region; scanning the sample and determining final fluorescence parameters based on said expected fluorescence parameters.

15 Claims, 3 Drawing Sheets (51) Int. Cl.
*G02B 21/16* (2006.01)
*G02B 21/36* (2006.01)

(56) References Cited

U.S. PATENT DOCUMENTS

| | | | |
|---|---|---|---|
| 2006/0129327 A1* | 6/2006 | Kim et al. | 702/19 |
| 2006/0226375 A1 | 10/2006 | Maruo | |
| 2007/0132998 A1* | 6/2007 | Tang et al. | 356/417 |
| 2011/0235875 A1* | 9/2011 | Filkins et al. | 382/128 |

OTHER PUBLICATIONS

D. Elson, et al.; "Time domain fluorescence lifetime imaging applied to biological tissue", Photochem. Photobiol. Sci. 3, 795-801 (2004).

D.S. Elson, et al.; "Fluorescence lifetime system for microscopy and multiwell plate imaging with a blue picosecond diode laser"; Optics Letters 12, 1409-1411 (2002).

International Search Report; PCT/EP2008/056672; Jul. 29, 2008.

J. Requejo-Isidro, et al.; "High-speed wide-field time-gated endoscopic fluoresence-lifetime imaging"; Optics Letters 29, 2249-2251 (2004).

M. Bouhifd, et al.; "Fluoresence imaging spectroscopy utilising acousto-optic tuneable filters"; 5826A-23 (OptoIreland, 2005).

M. Kress, et al.; "Time-resolved microspectrofluorometry and fluorescence lifetime imaging of photosensitizers using picosecond pulsed diode laser scanning microscopes"; Journal of Biomedical Optics 8, 26-32 (2003).

S. Pelet, et al.; "A Fast Global Fitting Algorithm for Fluorescence Lifetime Imaging Microscopy Based on Image Segmentation"; Biophysical Jourlan, vol. 87, 2807-2817 (2004).

Y. Zhang, et al.; "Simple Near-Infrared Time-Correlated Single Photon Counting Instrument with a Pulsed Diode Laser and Avalanche Photodiode for Time-Resolved Measurements in Scanning Applications"; Applied Spectroscopy 53, 497-504 (1999).

J.R. Lakowicz, "Principles of fluorescence spectroscopy" (Kluwer Academics, 1999).

T. Zimmermann, "Spectral imaging and linear unmixing in light microscopy", Adv. Biochem. Eng. Biotechnol. 95, pp. 245-265 (2005).

* cited by examiner

METHOD OF FLUORESCENCE IMAGING

TECHNICAL FIELD

The present invention generally relates to fluorescence imaging, and more particularly concerns fluorescence lifetime or spectrum imaging of biological samples.

BACKGROUND ART

Fluorescence imaging is a powerful technique for the analysis of biological samples. In the simplest case, an imaging system such as an epifluorescence microscope equipped with an excitation lamp and a filter-cube is used to illuminate the sample at one wavelength while imaging it at another.

However, significantly more information can be obtained from the same sample if the more advanced techniques of Hyper-Spectral Imaging (HSI) or Fluorescence Lifetime Imaging (FLIM) are employed. In a HSI setup the complete fluorescence spectrum is acquired for every point of the object. It is a particularly useful method to clearly discriminate different structural features within a sample when multiple fluorescent dyes are employed whose spectra overlap (T. Zimmermann, "Spectral imaging and linear unmixing in light microscopy," Adv. Biochem. Eng. Biotechnol. 95, 245-265 (2005)). Rather than measuring (spectral) intensity, FLIM involves the mapping of the decay times of fluorescence (J. R. Lakowicz, Principles of fluorescence spectroscopy (Kluwer Academics, 1999)), which can vary depending on the local environment of exogenous or endogenous fluorophores. Such a functional imaging approach is well suited to the study of biochemical and biophysical processes in tissues and cells, often in a non-destructive manner (D. Elson, J. Requejo-Isidro, I. Munro et al. "Time domain fluorescence lifetime imaging applied to biological tissue," Photochem. Photobiol. Sci. 3, 795-801 (2004)).

Wide-field spectral imaging is usually performed using a set of optical emission filters mounted on a filter wheel or rotary filter-cube holder. This approach is straightforward and relatively cheap, but is usually rather slow and cumbersome due to the mechanical switching of the filters. Typically only a limited number of spectral bands can be acquired which allows only partial separation of overlapping fluorescence spectra. More versatile HSI systems employ electro-optic devices such as Liquid Crystal Tunable Filters (LCTF), Linearly Variable band-pass Dielectric Filters (LVDF) or Acousto-Optical Tunable Filters (AOTF) (M. Bouhifd, M. P. Whelan, M. Aprahamian, "Fluorescence imaging spectroscopy utilizing acouto-optic tuneable filter", 5826A-23 (OptoIreland, 2005)). The LCTF solution offers approximately 30% of passband transmission efficiency, which is often unacceptable for low light-level applications. The LVDF resolution is roughly 15 nm, its spectral range covers 400-700 nm, and its transmission efficiency is around 40%. While these parameters are good enough for static imaging, using a LCTF for HSI to study dynamic behavior in low-light level conditions can be problematic. The AOTF is an electronically controllable, variable bandwidth optical filter, which provides significant versatility and performance in comparison to other tunable filters. It supports random access to any transmission-band or continuous spectral tuning and thus is very suitable for HSI when combined with a sensitive camera. However, all these wide-field HSI systems based on tunable filters can suffer from relatively poor image quality due to the scattering present in most biological samples. This can result in a decrease in image contrast and the loss of quantitative information, such as the concentration of a fluorophore.

As an alternative, reconstruction of a fluorescence map by making point-by-point measurements has proven to deliver images of superior quality (B. W. Pogue, S. L. Gibbs, B. Chen, M. Savellano, "Fluorescence Imaging in Vivo: Raster Scanned Point Source Imaging Provides More accurate Quantification then Broad Beam Geometries" Technology in Cancer Research and Treatment 3, 15-21 (2004)), which reveal more accurately the localization and concentration of fluorescent markers. However, since this approach usually requires raster scanning carried out by intricate electro-mechanical systems it is difficult and costly to implement.

Fluorescence lifetime imaging in the time-domain can generally be approached in two ways, namely wide-field fluorescence lifetime imaging or point-by-point raster scanning. Wide-field (or broad beam) imaging systems employ a Gated and Optical Intensified (GOI) camera in combination with a high-power pulsed laser. Typically, excitation light is irradiated on the area to be detected and fluorescence from the area is captured all at once by a CCD array sensor to thereby obtain fluorescence information of a two-dimensional region. Such a FLIM system is fast (J. Requejo-Isidro, J. McGinty, I. Munro, D. S. Elson et al. "High-speed wide-field time-gated endoscopic fluorescence-lifetime imaging," Optics Letters 29, 2249-2251 (2004)) but demonstrates lower temporal and spatial resolution in comparison to scanning measurements. The high cost and lack of portability are also issues, which have limited its uptake. On the other hand the successful demonstration of GOI-based FLIM using picosecond laser diodes has helped matters somewhat (D. S. Elson et. al., "Fluorescence lifetime system for microscopy and multiwell plate imaging with blue picosecond diode laser," Optics Letters 12, 1409-1411 (2002)).

Still with respect to wide-field imaging, since the fluorescence information of the image-taken area is detected as a whole at the same time—problems of image blurring due to light scattering may arise. Indeed, since the image pickup area is illuminated as a whole by a light source, detection and separation of weak fluorescence is difficult where there are multiple fluorescence spots around the weak point, because fluorescence light is scattered over the neighbourhood area, increasing background noise and overlapping the fluorescence to be measured. To avoid these problems, excitation light pattern generating devices have been developed that permit to irradiate different intensities and locations on a sample in sequence at relatively high frame rate. A fluorescence detecting apparatus using such excitation light pattern generating device, based on a digital micromirror device (DMD) or reflection-type liquid crystal device, is e.g. described in US 2006/0226375.

The second approach (scan-type) to time-domain FLIM exploits Time Correlated Single Photon Spectroscopy (TC-SPS) method combined with point-by-point scanning (Y. Zhang, S. A. Soper, L. R. Middendorf, J. A. Wurm, R. Erdmann, M. Wahl, "Simple Near-Infrared Time-Correlated Single Photon Counting Instrument with a Pulsed Diode Laser and Avalanche Photodiode for Time-Resolved Measurements in Scanning Applications," Applied Spectroscopy 53, 497-504 (1999)) or laser confocal scanning (M. Kress, T. Meier, R. Steiner, F. Dolp, R. Erdmann, U. Ortmann, A. Rück, "Time-resolved microspectrofluorometry and fluorescence lifetime imaging of photosensitizers using picosecond pulsed diode lasers in laser scanning microscopes," Journal of Biomedical Optics 8, 26-32 (2003)). Typically a punctual light beam of excitation light irradiates the sample so that the fluorescence from the irradiated spot is detected by e.g. a Photo-Multiplier Tube (PMT), and this irradiation and detection scanning throughout the object to be observed allows to obtain fluorescence information of a two-dimensional area.

Picosecond laser diodes are the most popular excitation source because of their compactness and reasonable cost, while a PMT or an Avalanche Photo-Diode (APD) may be used to detect the emitted fluorescence photons. With respect to wide-field FLIM, scanning-TCSPS is more straightforward and less expensive to implement. It also offers higher temporal resolution, but at the price of much slower imaging rates. To obtain FLIM images, either the sample is moved on a translation stage under the excitation light spot or the sample is held steady while the excitation spot is raster-scanned using galvano-mirrors. Although a number of attractive commercial solutions exist based on both scanning methods, the disadvantages of point scanning in general are its low imaging rate and the lack of flexibility in how an image is formed. Normally a minimum sampling time of 100 μs required per measurement point (pixel), thus leading to a duration of several seconds to tens of minutes to acquire a complete image. The actual duration depends on a number of factors including the strength of the fluorescence signal and the desired field of view, temporal and spatial resolution. Most scanning systems are analogue by nature and thus neither offer random access to any point or region of interest on the sample, nor the possibility to bin or combine the photons emitted from different locations.

An important issue in FLIM/HIS imaging is of course also the accuracy of data analysis. To reduce the acquisition time and full image frame reconstruction, data acquisition time per single pixel is typically reduced, which in turn reduces signal to noise ratio and further decreases the accuracy and reliability of data processing. By the extreme or complex nature of the phenomena observed the data analysis itself is also complex and time consuming. Namely, to adjust phenomenological parameters in the photo-physical model to reach; satisfying agreement between experimental dataset and the model, one needs to perform iterative data fitting. To keep high spectral/temporal resolution of measurements, large dataset/pixel are produced and large number of pixels; need to be analysed to reconstruct the FLIM/HSI image. Thus the fitting algorithm is extremely time consuming. Number of methods has been proposed to decrease the computational time, which are based on the so-called "Global Analysis Approach". Most commonly the fluorescence signals from all the pixels are post-processed by summing all together to increase S/N ratio. The result, i.e. the phenomenological parameters of the model are then used as initial parameters for data analysis algorithm performed off-line (i.e. after fluorescence data acquisition) for every single spatial location on the sample. Modifications of the Global Analysis include dataset summation from quarters of the image or from manually chosen regions based on white light anatomical image of the sample [S. Pelet, M. J. R. Previte, L. H. Laiho, P. T. C. So, "*A fast global fitting algorithm for fluorescence lifetime imaging microscopy based on image segmentation*", Biophysical Jourlan, vol. 87, 2807-2817 (2004)]. These methods suffer however either from loosing details (weak signal and its impact to the overall fluorescence is weak) or the need for high experience in manual marking the desired regions of interest and their use is limited to specific cases. Moreover the data analysis is performed off-line, having the dataset per every pixel already acquired.

JP 2006 171024 A describes a multi-point fluorescence spectrophotometry method using a DMD, wherein a sample is illuminated to excite its fluorescence and an image thereof is acquired; image segmentation is based on the existence of fluorescence (e.g. using a luminance threshold); and the fluorescence of each Region of Interest is acquired one by one.

BRIEF SUMMARY OF THE INVENTION

The disclosure provides an alternative fluorescence imaging method.

According to a first aspect of the present invention, a method of fluorescence imaging comprises the steps of:
a) illuminating a sample to excite its fluorescence and acquiring an image thereof;
b) based on spectral and spatial information from the sample's fluorescence image, segmenting the image into regions of similar spectral properties;
c) for each image segment, exciting the fluorescence of the corresponding sample region, and detecting the corresponding fluorescence;
d) based on modelling, determining expected fluorescence parameters from the fluorescence signals detected for each region;
e) scanning the sample and determining final fluorescence parameters based on said expected fluorescence parameters.

The present method thus proposes a (raster) scanning fluorescence imaging method, which comprises a preliminary step of fluorescence image acquisition and analysis, in order to discriminate different structural and functional sample regions, before proceeding with the sample scanning per se. This method is particularly well suited for FLIM or HSI imaging. The discrimination is performed by so-called "segmentation" of the fluorescence image, respectively of the sample, based on fluorescence spectral and spatial information that may be gained with any spectrally resolved imaging method. Trained good initial parameters, i.e. the expected fluorescence parameters, are then determined for each region (segment) using mathematical models and these good initial parameters will subsequently be used to determine the final fluorescence parameters of the fluorescence signals acquired during the raster scanning step e). Typically, the final fluorescence parameters to be determined upon raster scanning can be determined by a fitting algorithm using the expected fluorescence parameters as initial parameters.

By this segmentation step, a priori information can be provided that will speed-up the fitting algorithms traditionally employed to determine fluorescence parameters by raster scanning. Indeed, as is well known in the art, the process of FLIM or HSI image analysis is usually performed by iterative fitting of the experimental data with mathematical models. The image segmentation and provision of expected fluorescence parameters permits to have a good initial parameters for the decay (for FLIM) or spectra (for HSI) fitting algorithms that are used to determine the parameters of the fluorescence signals acquired during raster scanning.

The present method thus significantly differs from conventional scanning FLIM where data analysis is performed off-line without any a priori information and thus using random initial parameters in the fitting algorithms. Moreover the proposed method supplies Good Initial Parameters for further faster and more accurate data analysis based on information gained from photo-physically similar regions, which could be called Local Analysis, in opposite to Global Analysis algorithms which average the fluorescence signal and loose details.

Still with respect to segmentation, one may further take into account the detected fluorescence intensities in addition to their fluorescence spectra to determine the similar sample regions. This segmentation procedure is to be distinguished from image acquisition and processing under white light, where the sample fluorescence is not evoked to classify different anatomical regions.

Scanning step e) involves scanning an excitation light spot over the sample and detecting fluorescence signals (fluorescence decay or fluorescence spectrum) using dedicated equipment. For FLIM imaging, the fluorescence can be detected by a photomultiplier, a photodiode or the like, that permits recoding the temporal profile of fluorescence intensities by any method (e.g. TCSPS, fluorescence intensity vs. time, etc.). For HSI the fluorescence detection is performed by means of a spectrally selective detector based on any technology (e.g. spectrophotometer, set of spectrally resolvable photodiodes/photomultipliers etc.), to record the fluorescence intensities at different wavelengths.

Preferably, the excitation light pattern generating device comprises a digital micromirror device (DMD). Such a spatial illuminator is compact and does not comprise any macro mechanical moving parts. The DMD can easily be controlled to reflect excitation light at any 2D area (region) on the sample to perform the localised fluorescence analysis of step c). In addition, the DMD can advantageously be controlled to generate a moving excitation light spot in order to perform the raster scanning of excitation light in step e), which is a kind of illumination pattern. Although a DMD is preferred for its ease of control, costs and reliability, one can use other spatial illuminators, e.g. a Liquid Crystal Transmittive or Reflective matrices. Steps c) and e) can even be performed with different devices.

According to a second aspect of the present invention, a method of fluorescence imaging comprises the steps of:
  a) illuminating a sample to excite its fluorescence and acquiring an image thereof;
  b) based on spectral and spatial information from the sample's fluorescence image, segmenting the image into regions of similar spectral properties;
  c) for each image segment, exciting the fluorescence of the corresponding sample region, and detecting the corresponding fluorescence;
  d) based on modelling, determining fluorescence parameters from the fluorescence signals detected for each region;
  e) constructing fluorescence lifetime or fluorescence spectrum images providing a map of the fluorescence parameters corresponding to said fluorescence parameters of step d.

The first steps a)-d) of this method are identical to those described for the first method, however there is no raster scanning. The present inventors have indeed found that in some circumstances, a map (image) of fluorescence image constructed with fluorescence information obtained at step d) is sufficient. This can be performed for lifetime but also for spectral fluorescence parameters.

In the case of fluorescence lifetime imaging, the present invention may be called segmented fluorescence lifetime imaging or "SFLIM". Compared to traditional scan-type FLIM, it is of course not as precise but extremely faster. In the case of fluorescence spectra imaging, the present invention may be called segmented fluorescence hyper spectral imaging or "SHSI". Compared to traditional scan-type HSI, it is of course not as precise but extremely faster.

It shall be appreciated that in both methods, image segmentation is based on the spectral properties of the sample. Intensity can be used in addition to spectral discrimination. In one embodiment, the sample spectral properties are coded as a colour (Hue) of the imager pixels. In the case of a colour CCD camera, the composition of e.g. RGB components within a single pixel provides information sufficient to distinguish between e.g. more green from more blue regions. As it will appear to those skilled in the art, a diversity of methods of acquiring colour images may be used for segmentation, as long as they provide spatially resolved spectral information in order to distinguish between regions exhibiting similar photophysical properties; typically useful images pixels may be coded as a intensity in a given spectral range.

As it has been understood, the present inventive methods are particularly useful for FLIM, a technique (used mainly in biology) of mapping the fluorescence lifetime of chromophores (endogenous like e.g. porphyrins, proteins, collagen, etc. or exogenous like e.g. fluorescent labels, staining dies) located within living/stained cells. FLIM imaging involves a lot of computation, since the fluorescence lifetime (described by the (multi)exponential decay) for every single pixel should be measured and converted to a decay constant by fitting the experimental decay to the model.

The present method also finds particular application to HSI imaging, a technique (used in biology, medicine, satellite imaging for agriculture purposes) of collecting the images within different spectral (UV-Vis-IR) regions. The simplest case is using a glass color filter to acquire an intensity image for chromophores emitting in e.g. red in opposite to all other emitters present in the object. Most sophisticated solution engage measuring full fluorescence spectrum (e.g. Intensity profile vs. wavelength of emission) for every single pixel. To analyze the HSI images reliably (in a quantitative way by e.g. measuring the concentration ratio of the two chromophores exhibiting different spectral features) one needs a lot of computation, since the experimental spectra need to be deconvoluted—decomposed into the spectra of each chromophore available in the sample. The HSI imaging and decomposition of full fluorescence spectrum is especially useful when number of fluorophores exhibiting different but overlapping fluorescence spectra are present within the same spatial location (pixel).

The present methods will prove much faster and more accurate than conventional approaches in these techniques of FLIM and HSI, where there is typically no a priori information before raster scanning.

As it will be understood, the method of the invention will typically be implemented in a computer-controlled optical apparatus. Therefore, the present invention also concerns a computer program and a computer program product comprising computer program code means (possibly on a computer readable medium) adapted to perform the above methods.

According to a further aspect of the present invention, there is proposed a fluorescence imaging system for analysing a sample comprising:
  an excitation light source;
  an excitation light pattern generating device illuminated by said excitation light source and able to produce light patterns onto a sample to be analysed;
  an imaging device producing whole-field fluorescence images with spectral information;
  a photodetector for detecting whole-field fluorescence emitted by the sample;
  Programmable control means for controlling said excitation light pattern generating device and acquiring experimental data from said imaging device and photodetector.

BRIEF DESCRIPTION OF THE DRAWINGS

The present invention will be more apparent from the following description of several not limiting embodiments with reference to the attached drawings, wherein:

FIG. 3: is a schematic representation of the segmentation step of the Local Analysis FLIM imaging algorithm. Based on colour fluorescence image I(x,y) and further segmentation of the Hue histogram, binary masks $B_r$ are created and successively sent to DMD projector. Experimental decays $D_r$ are simultaneously collected for every binary pattern projected on the sample. After analysis i.e. fitting (Fit) of experimental decay $D_r$ with initial parameters P, a reference table $T_r = \{A^r, \tau^r_1, \tau^r_2\} = \text{Fit}(D_r, P)$ is created. Simultaneously a reference map $S_{x,y}$ is created $S_{x,y} = r$, where all pixels belonging to the binary mask $B_r$ get the same number (r), that reference to the reference table $T_r$. Thus for every pixel (x,y) one can easily get estimated fluorescence parameters, e.g. $\tau_{x,y} = T^\tau_{S_{x,y}}$.

DETAILED DESCRIPTION OF PREFERRED EMBODIMENTS

A preferred embodiment of the present method will now be described in more detail, as applied to raster-scanning FLIM with prior fluorescence image acquisition and analysis, in order to discriminate different structural and functional sample regions. The discrimination is performed by segmentation of a wide field fluorescence image (whole sample) based on fluorescence spectral and spatial information gained with any spectrally resolved imaging method. The goal of the method is to supply fluorescence decay fitting algorithms (in the case of FLIM) or fluorescence spectra fitting algorithms (in the case of HSI) with trained Good Initial Parameters to increase the accuracy and speed of FLIM/HSI image reconstruction.

Figure 1:
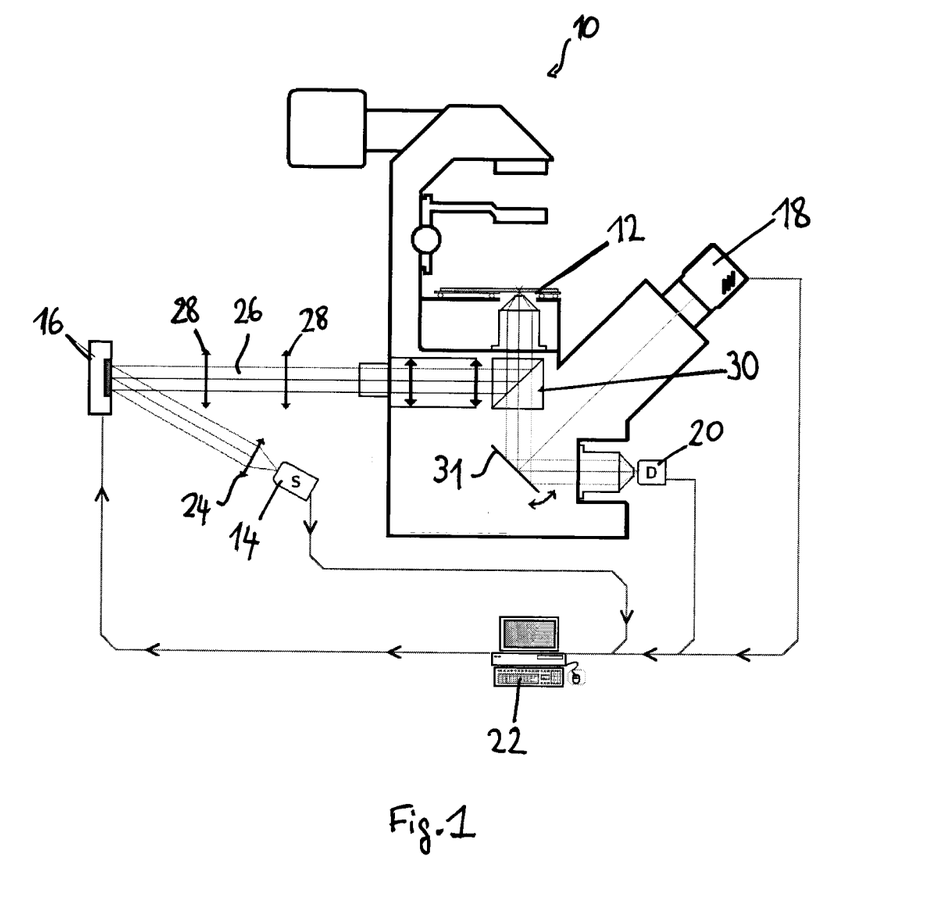
FIG. 1: is a sketch of the laboratory optical set-up for implementing the present fluorescence imaging methods.

A preferred experimental setup for this method is illustrated in FIG. 1. It comprises e.g. microscope-type device 10 on which the sample to be analysed is supported on a stage, a light source 14 emitting excitation light—e.g. a pulsed laser diode ($P_{max}=1$ mW, $t_{FWHM}=50$ ps, LDH 405) working with 40 MHz repetition rate with PDL 800-B pulsed laser diode driver from PicoQuant GmbH—an excitation light pattern generating device 16, an imaging sensor 18 (e.g. colour CDD array), a photodetector 20 and a computer 22. Light emitted by the light source 14 is collected by conditioning optics 24 and falls on the excitation light pattern generating device 16, which is advantageously formed by a digital micromirror device (DMD) with appropriate control electronics (here a 0.7 XGA 1024×768 pixels DMD chip by Texas Instruments) controllable via the computer 22. Preferably conditioning optics 24 include a beam expander and anamorphic prism to condition the excitation light beam and to illuminate homogenously the DMD 16. Reference 26 indicates an illumination path extending from the DMD to the sample 12. The light reflected by the DMD mirrors 16, i.e. the DMD image projected through the conditioning optics 28, is guided through the back illumination port of the microscope 10 and a filter cube 30 to the back surface of the sample 12.

In the setup of FIG. 1, the wide field fluorescence is transmitted by a respective high pass dichroic filter in the filter cube 30 and reflected by a tiltable mirror 31 either onto the CCD imager 18 or the photomultiplier tube 20.

It shall be appreciated that the use of a DMD as spatial illuminator not only permits to produce excitation patterns but also, when properly programmed, allows raster-type, point-by-point scanning. Raster scanning can indeed be performed by sequentially switching single pixel (or rectangular bin of pixels) from OFF into the ON state. In the ON state, the selected group of micro-mirrors is deflected to reflect the excitation light, through the optics and filter cube to the sample. The excitation light reflected from all other micromirrors (in OFF state) is then damped and does not cause any fluorescence of the sample. During spot illumination of the sample, the fluorescence spectrum or fluorescence lifetime is recorded and preferably on-line processed to FLIM images as described below. Next the pixel(s) is switched OFF and the adjacent micro-mirror (or a group of micromirrors) is turned ON to illuminate the adjacent sample region. Since acquired fluorescence signal is correlated with the DMD pixel or group of pixels by spatially localized illumination spot, respective reconstruction image pixels can be filled in with the on-line processed fluorescence information.

Figure 2:
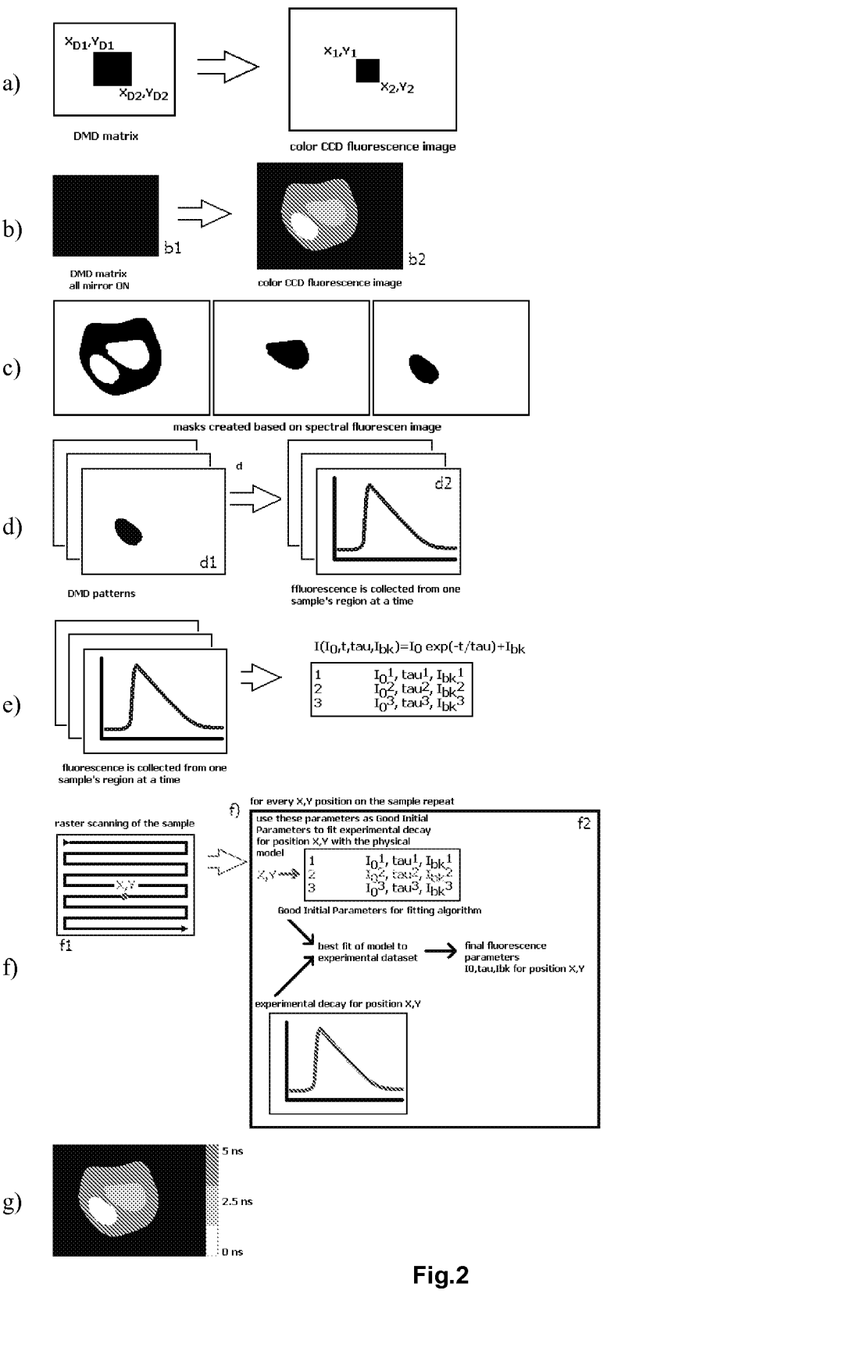
FIG. 2: is a principle drawing illustrating the main steps of the present method.

The principle of the present method can be rapidly understood on the basis of FIG. 2. First, a calibration step is advantageously carried out to establish a correlation between the specimen/sample and the DMD 16, which permits to precisely know the sample coordinates (in the imager) corresponding to those of the DMD 16, as shown in FIG. 2a. The result is thus a transfer function that gives the correspondence between mirror coordinates on the DMD and the projected light spot coordinates on the sample.

Next, the whole sample is illuminated (DMD matrix all mirrors ON, image b1 in FIG. 2b) to excite its fluorescence and a preview image is acquired by means of the CCD imager. Image segmentation is subsequently performed on the basis of the spatial and spectral information gained from the preview image, to determine regions in the sample exhibiting similar photo-chemo-physical properties. It is clear that here a region/segment is typically a sub-area from the whole sample area. In the preview image, a segment will typically consist of a plurality of neighbouring pixels in the CCD fluorescence image b2 of FIG. 2b). Hence the term "segment" designates a part of the image having similar spectral properties (typically pixels of similar colour or grey level) that is less than the whole image area but more than one unit area (pixel) of the image. And by "segmentation" is understood the determination of the segments on the basis of spectrum information, optionally with corresponding intensities.

Upon identification of the different segments (or regions of interest), the coordinates of these regions are used to build so-called "masks" (shown in FIG. 2c for ease of understanding) that will permit illuminating the corresponding sample regions. Accordingly, using these masks to control the respective DMD mirrors position (ON or OFF) the different sample regions are selectively illuminated (normally one after another) with the DMD (DMD mask pattern d1 in FIG. 2d) and the corresponding fluorescence emitted by the excited region is detected (image d2). Indeed, due to the transfer function initially determined (FIG. 2a), it is possible to precisely illuminate a region of the sample, so that fluorescence is only evoked in that precise region. For FLIM imaging, a photodetector is used to record the emitted fluorescence vs. time, whereas for HSI imaging a spectrophotometer is used to record the fluorescence intensity vs. wavelength. In this step the measure is a kind of average value over the excited sample area, since it does not provide spatially resolved fluorescence information but simply global records of the fluorescence emitted by the excited area.

Next (FIG. 2e) the acquired experimental data are fitted with a mathematical model to extract key parameters (e.g. decay constant, peak position or width of the spectral band, etc.) as good initial parameter for further analysis. This is done for each segment/region.

In the case FLIM, fitting can e.g. be done with single exponential models, in which case Tau (decay constant) is of interest, possibly with $I_0$, $I_{bk}$. For HSI, fitting can be done with e.g. Gaussian models, where central wavelength and width of spectral band are parameters of interest. There is however a variety of photophysical models and methods to be used for data analysis.

The DMD is then controlled by the computer to perform raster scanning (FIG. 2f, image f1) of the whole sample, the previously determined good initial parameters (FIG. 2e) are used in the subsequent data processing of the raster scanned experimental data to determine the final and accurate fluorescence parameters. Again, these final parameters (here decay parameters $I_0$, Tau and $I_{bk}$) for each imager position are determined by iterative fitting (block f2).

Finally, a FLIM image (FIG. 2g) is reconstructed showing the maps of the final fluorescence parameters (e.g. Tau-decay constant) across the sample.

As it is clear for those skilled in the art, in the scanning step f) the excitation light spot is limited in size to illuminate a very small spot on the sample, whereas in the segmentation step d) comparatively much larger areas are typically illuminated by the DMD.

Further Example

A more detailed example of raster scanning FLIM imaging will now be explained with respect to FIGS. 3 and 4. As previously explained, preliminary calibration is preferably performed to establish a spatial correlation between the specimen/sample and the DMD, which permits to precisely know the sample coordinates (in the imager) corresponding to those of the DMD. This is achieved by e.g. projecting a rectangle defined by a pair of DMD coordinates ($X_1^{DMD}, Y_1^{DMD}$; $X_2^{DMD}, Y_2^{DMD}$) onto the homogenously fluorescent sample. Extracting the rectangle corners ($X_1^F, Y_1^F; X_2^F, Y_2^F$) on the fluorescence image acquired with the camera, allows to convert coordinates on the plain sample to respective DMD mirrors coordinates and opposite. This step permit and advantageous control of further data acquisition and analysis.

In the next step, a fluorescence image of the whole sample is acquired. This is achieved by switching all the DMD mirrors to the ON position for the time required to record the fluorescence image. The fluorescence steady-state image I(x, y) (x=0 . . . 1024, y=0 . . . 768) is acquired in order to gain spatial distribution of spectral-information and this can be achieved either with high-pass dichroic filter and color camera, or black&white camera combined with a set of 2 or more bandpass dichroic filters, intensified camera combined with a tunable bandpass filter or any other spectrally imaging device. The image can typically be acquired within a few tens of microseconds (stained samples) up to a few seconds (autofluorescence).

Figure 3:
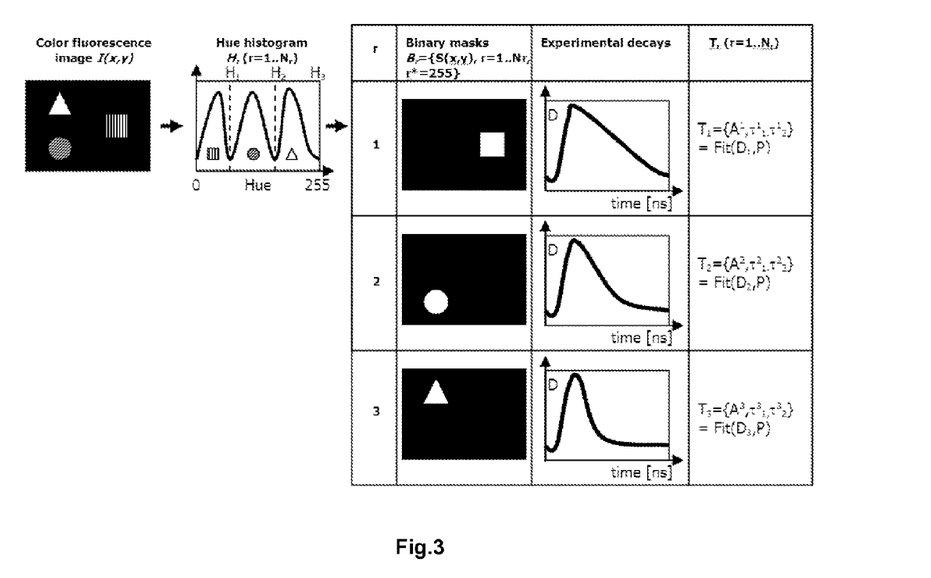
Figure 4:
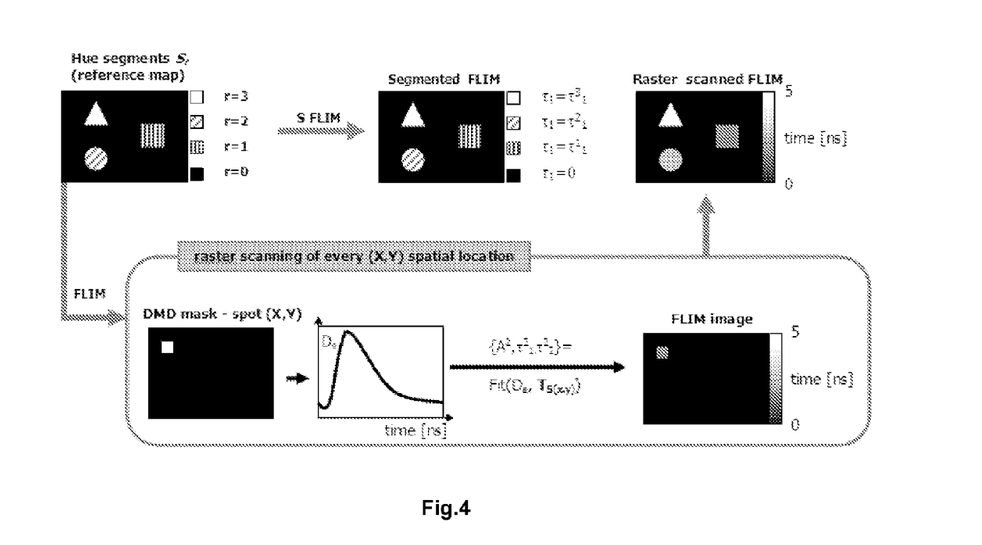
FIG. 4: is a schematic representation of the imaging step of the Local Analysis FLIM imaging algorithm. Every image pixel refers to the reference table $T_r$ (see FIG. 3) by the value S(x,y). One way of data analysis is Segmented FLIM imaging, where the pixels of FLIM image F(x,y) take over their values directly from $T_r$ table $F(x,y) = T_{S(x,y)}$. The other analysis approach (raster scanned FLIM) treats $T_{S(x,y)}$ values as Good Initial Parameters for further raster scanning $F(x,y) = \text{Fit}(D, T_{S(x,y)})$ performed for very pixel.

For the sake of exemplification, let us consider an example of steady-state fluorescence image I(x,y) on FIG. 3, acquired with a high-pass filter and a color CCD camera. The HSL (Hue-Saturation-Luminance) colour space may be considered, since spectral information (Hue) is separated from intensity (Luminance) plane. The Hue histogram represents hue components available in the image and by subdividing the histogram into a $N_r$ number of hue classes $H_r$ (r=1 . . . $N_r$−1, $H_0$=0, $H_{Nr}$=255, $H_r$<$H_{r+1}$) one can mask regions, where the sample exhibits similar spectral properties. Within single Hue class, intensity segmentation may be additionally performed, but to keep explanation simple, we will focus on hue segmentation only. A map (of the size of the DMD matrix size) of Hue segments $S_r$={S(x,y)=r; r=1 . . . $N_r$} is created and every pixel within the map is attributed to a defined hue class with the following algorithm $$\text{for } (r = 1; r < N_r; r = r + 1) \quad (1)$$

$$S(x, y) = \begin{cases} 0 & I(x, y) > H_r \cap I(x, y) \leq H_{r-1} \\ r^* & H_{r-1} < I(x, y) \leq H_r \end{cases}$$

where r is the index of successive Hue range, and $H_r$ designates edges of that ranges.

Additionally binary masks are created $B_r$ (r=1 . . . $N_r$), which are the collections of pixels belonging to the same Hue range $B_r$={S(x,y)=r}, where r* in equation Eq.1 takes '255' value (corresponding to DMD pixel ON state).

The binary masks are then sequentially sent to the DMD illuminator (FIG. 3 table), respective segments on the sample are excited and simultaneously the fluorescence photons are recorded. By analysing the sample segment by segment, $N_r$ number of decay histograms are collected and analyzed to extract decay constants $\tau_r$ and to create reference table $T_r$ containing expected decay model parameters $T_r$={$\tau_r$} (r=1 . . . $N_1$). In the case of two exponent decays, any other parameters (like A-ratio between short and long component, values of short $\tau_i$ and long $\tau_2$ decay constants $T_r$={A, $\tau_1, \tau_2$}) that reliably model experimental dataset within the mask, can be extracted and stored. In this way Hue segments $S_r$ and in consequence every single pixel (x,y) refers to the $T_r$ table. The parameters stored in the $T_r$ table are the values fitted from fluorescence decay histograms that are averaged over the pixels defined by the $B_r$ masks (the term "averaged" here means that it is one value for a region and is not to be understood in a statistical sense).

Upon determination of the expected decay parameters, raster scanning of the whole sample is performed (FIG. 4. branch FLIM) to determine more precise and spatially resolved fluorescence lifetime parameters using the previously determined expected decay parameters as Good Initial Parameters.

With respect to the present example, the decay model parameters stored in T, table serve as Good Initial Parameters (GIP) for further pixel-by-pixel raster-scanning and on-line fitting and analysis. Switching the (x,y) DMD mirror ON allows to collect the fluorescence decay histogram $I_{exp}(x,y,t)$. Initial fitting parameters can be referred by $T_{S(x,y)}$. It was already demonstrated, that fitting algorithms supplied with GIP converge to reliable solutions much faster then in untrained (full-guess) case. Since model decay curves $$I_m^i(t) = [A \cdot \exp(-t/\tau_1^i) + (1-A) \cdot \exp(-t/\tau_2^i)] \otimes IRF(t, t_0) \quad (2)$$

for all (i=1 . . . $N_s$) segments and all pixels ($I^{S(x,y)}_m$) are known prior to raster scanning (due to step presented in FIG. 3) one can precede the fitting step with solving a linear problem $$I_{exp}(x,y,t) = c(x,y) \cdot I_m^S(x,y)(t) + I_{bk}(x,y) \quad (3)$$

Finding c(x,y) constant by solving $$c(x, y) = \left\langle \frac{I_{exp}(t) - I_{bk}(x, y)}{I_m^{S(x,y)}(t)} \right\rangle \quad (4)$$

allows to calculate also goodness of fit (GOF) between the model and experimental decay. When the obtained GOF is satisfying, no further steps are required and $A(x,y)=T^A_{S(x,y)}$, $\tau_1(x,y)=T^{\tau 1}_{S(x,y)}$, $\tau_2(x,y)=T^{\tau 2}_{S(x,y)}$. Otherwise the numbers stored in T, table serve as GIP for further iterative convolution fitting. A Fit($D_t,P=\{A,\tau_1,\tau_2\}$) procedure delivers best fitted decay model by optimizing a set of coefficients $\{A, \tau_1, \tau_2\}$ to minimize GOF parameters defined as $$GOF(P) = \frac{1}{N} \cdot \sum_{t=1...N} \frac{(D_t - \text{Fit}(D_t, P))^2}{D_t} \quad (5)$$

where $D_t$ is experimental decay histogram.

In another example the procedure described above is the same, but the expected fluorescence parameters gathered as presented on FIG. 3 are used as final fluorescence parameters (FIG. 4, branch SFLIM) and no further raster scanning is performed.

The invention claimed is:

1. Method of fluorescence imaging of a sample comprising:
  a) illuminating the whole sample with a digital micromirror device (DMD) illuminator to excite its fluorescence; acquiring a preview image of the sample and establishing a correlation of the coordinates of the preview image with the coordinates of the components of the DMD, wherein the DMD is connected to a detector via a computer;
  b) based on fluorescence spectral and spatial information from the preview image, segmenting the preview image into segments of similar spectral properties, thereby obtaining a plurality of image segments, wherein each image segment of the plurality of image segments corresponds to a sub-area of the whole sample region;
  c) building plurality of masks using coordinates of the components of the DMD corresponding to the sub-areas of the sample region corresponding to the image segments;
  d) using the mask of each image segment, selectively and sequentially exciting fluorescence of each of the sub-areas of the sample region corresponding to the image segments, and detecting fluorescence signals for the sub-areas of the sample region;
  e) based on mathematical modeling, determining expected fluorescence parameters comprising expected fluorescence decay parameters or expected fluorescence spectrum parameters from the detected fluorescence signals of each sub-area of the sample region; and
  f) scanning the whole sample again and determining final fluorescence parameters comprising final fluorescence lifetime parameters or final fluorescence spectrum parameters by using fitting algorithm that use the expected fluorescence parameters determined at step e) as good initial parameters.

2. Method according to claim 1, wherein step (f) involves scanning the whole sample using a punctual, excitation light beam, and detecting the emitted fluorescence by means of a photodetector dedicated for fluorescence lifetimes or fluorescence spectra detection.

3. Method according to claim 1, wherein step (f) involves raster scanning the whole sample using a punctual, excitation light beam, and detecting the emitted fluorescence by means of a photodetector dedicated for fluorescence lifetimes or fluorescence spectra detection.

4. Method according to claim 1, wherein said scanning step (f) involves detecting spectral and/or intensity information and/or fluorescence temporal information and/or fluorescence polarisation information for each scanned point.

5. Method according to claim 3, wherein said scanning step (f) involves detecting spectral and/or intensity information and/or fluorescence temporal information and/or fluorescence polarisation information for each scanned point.

6. Method according to claim 1, wherein step (d) involves illuminating each region by means of an excitation light pattern generating device and detecting the emitted fluorescence by means of a photodetector generating said fluorescence signals.

7. Method according to claim 1, comprising a preliminary calibration step, wherein a spatial correlation is established between the area that is illuminated by the excitation light pattern generating device and the corresponding detected preview image.

8. Method according to claim 1, wherein segmentation step b) is additionally based on detected intensities.

9. Method according to claim 1, comprising the additional step (g) of constructing an image of fluorescence lifetime or fluorescence spectrum providing a map of the final fluorescence parameters for the analysed sample.

10. A fluorescence imaging system structured to analyze a sample according to the method of claim 1, the system comprising:
  an excitation light source;
  an excitation light pattern generating device comprising a digital micromirror device (DMD) illuminated by said excitation light source and able to produce light patterns onto a sample to be analysed;
  an imaging device producing whole-field fluorescence images with spectral information;
  a photodetector for detecting fluorescence emitted by an excited spot or region on the sample;
  programmable control means for controlling said excitation light pattern generating device and acquiring experimental data from said imaging device and photodetector.

11. Method of fluorescence imaging of a sample comprising:
  a) illuminating the whole sample with a digital micromirror device (DMD) illuminator to excite its fluorescence; acquiring an image of the sample and establishing a correlation of the coordinates of the image with the coordinates of the components of the DMD, wherein the DMD is connected to a detector via a computer;
  b) based on fluorescence spectral and spatial information from the sample's fluorescence image, segmenting the image into segments of similar spectral properties, wherein each image segment corresponds to a sub-area of the sample region;
  c) building a plurality of masks using coordinates of the components of the DMD corresponding to the sub-areas of the sample region corresponding to the image segments;
  d) using the mask for each image segment, selectively and sequentially exciting the fluorescence of the corresponding sub-areas of the sample region, and detecting the corresponding fluorescence;

e) based on mathematical modelling, determining expected fluorescence parameters comprising expected fluorescence decay parameters or expected fluorescence spectrum parameters from the fluorescence signals detected for each sub-area of the sample region corresponding to each image segment; and f) constructing fluorescence lifetime images or fluorescence spectrum images providing a map of the fluorescence parameters corresponding to said expected fluorescence parameters of step (e).

12. A computer program comprising computer program code means adapted to perform a method of fluorescence imaging of a sample, the method comprising:

a) illuminating the whole sample with a digital micromirror device (DMD) illuminator to excite its fluorescence; acquiring a preview image of the sample and establishing a correlation of the coordinates of the preview image with the coordinates of the components of the DMD, wherein the DMD is connected to a detector via a computer;

b) based on fluorescence spectral and spatial information from the preview image, segmenting the preview image into segments of similar spectral properties, thereby obtaining a plurality of image segments, wherein each image segment corresponds to a sub-area of the whole sample region;

c) building plurality of masks using coordinates of the components of the DMD corresponding to the sub-areas of the sample region corresponding to the image segments;

d) using the mask of each image segment selectively and sequentially exciting fluorescence of each of the sub-areas of the sample region corresponding to the image segment, and detecting fluorescence signals for the sub-areas of the sample region;

e) based on mathematical modelling, determining expected fluorescence parameters comprising expected fluorescence decay parameters or expected fluorescence spectrum parameters from the detected fluorescence signals of each sub-area of the sample region;

f) scanning the whole sample again and determining final fluorescence parameters comprising final fluorescence lifetime parameters or final fluorescence spectrum parameters by using fitting algorithm that use the expected fluorescence parameters determined at step (e) as good initial parameters , wherein said program is run on a computer.

13. A computer program product comprising program code means stored on a computer readable medium for performing a method of fluorescence imaging of a sample, the method comprising:

a) illuminating the whole sample with a digital micromirror device (DMD) illuminator to excite its fluorescence; acquiring a preview image of the sample and establishing a correlation of the coordinates of the preview image with the coordinates of the components of the DMD, wherein the DMD is connected to a detector via a computer;

b) based on fluorescence spectral and spatial information from the preview image, segmenting the preview image into segments of similar spectral properties, thereby obtaining a plurality of image segments, wherein each image segment corresponds to a sub-area of the whole sample region;

c) building a plurality of masks using coordinates of the components of the DMD corresponding to the sub-areas of the sample region corresponding to the image segments;

d) using the mask of each image segment selectively and sequentially exciting fluorescence of each of the sub-areas of the sample region corresponding to the image segments, and detecting fluorescence signals for the sub-areas of the sample region;

e) based on mathematical modeling, determining expected fluorescence parameters comprising expected fluorescence decay parameters or expected fluorescence spectrum parameters from the detected fluorescence signals of each sub-area of the sample region;

f) scanning the whole sample again and determining final fluorescence parameters comprising final fluorescence lifetime parameters or final fluorescence spectrum parameters by using fitting algorithm that use the expected fluorescence parameters determined at step (e) as good initial parameters, when said program product is run on a computer.

14. A computer program comprising computer program code means adapted to perform a method of fluorescence imaging of a sample, the method comprising:

a) illuminating the whole sample with a digital micromirror device (DMD) illuminator to excite its fluorescence; acquiring a preview image of the sample and establishing a correlation of the coordinates of the preview image with the coordinates of the components of the DMD, wherein the DMD is connected to a detector via a computer;

b) based on fluorescence spectral and spatial information from the preview image, segmenting the preview image into segments of similar spectral properties, thereby obtaining a plurality of image segments, wherein each image segment corresponds to a sub-area of the sample region;

c) building a plurality of masks using coordinates of the components of the DMD corresponding to the sub-areas of the sample region corresponding to the image segments;

d) using the mask of each image segment selectively and sequentially exciting fluorescence of the corresponding sub-areas of the sample region, and detecting the corresponding fluorescence;

e) based on mathematical modelling, determining expected fluorescence parameters comprising expected fluorescence decay parameters or expected fluorescence spectrum parameters from the fluorescence signals detected for each sub-area of the sample region corresponding to each image segment; and f) constructing fluorescence lifetime images or fluorescence spectrum images providing a map of the fluorescence parameters corresponding to said fluorescence parameters of step (e), when said program is run on a computer.

15. Method of fluorescence imaging of a sample comprising:

a) illuminating the whole sample with a digital micromirror device (DMD) illuminator to excite its fluorescence; acquiring a preview image of the sample and establishing a correlation of the coordinates of the preview image with the coordinates of the components of the DMD, wherein the DMD is connected to a detector via a computer;

b) based on fluorescence spectral and spatial information from the preview image, segmenting the preview image into segments of similar spectral properties, thereby obtaining a plurality of image segments, wherein each image segment of the plurality of image segments corresponds to a sub-area of the whole sample region;

c) building plurality of masks using coordinates of the components of the DMD corresponding to the sub-areas of the sample region corresponding to the image segments;

d) using the mask of each image segment, selectively and sequentially exciting fluorescence of each of the sub-areas of the sample region corresponding to the image segments, and detecting fluorescence signals;

e) based on mathematical modeling, determining expected fluorescence lifetime parameters comprising expected fluorescence decay constants from the detected fluorescence signals of each sub-area of the sample region;

f) scanning the whole sample again and determining final fluorescence lifetime parameters comprising final fluorescence decay constant by using fitting algorithm that use single exponential model and the expected fluorescence parameters determined at step e) as good initial parameters; and constructing fluorescence lifetime images providing a map of the final fluorescence lifetime parameters.

* * * * *